(12) United States Patent
Lauer

(10) Patent No.: US 6,752,172 B2
(45) Date of Patent: Jun. 22, 2004

(54) DISPOSABLE CASSETTE HAVING A SEALING MEMBRANE AND A VALVE ACTUATOR THEREFOR

(75) Inventor: Martin Lauer, St. Wendel (DE)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 15 days.

(21) Appl. No.: 09/984,160

(22) Filed: Oct. 29, 2001

(65) Prior Publication Data
US 2002/0062109 A1 May 23, 2002

(30) Foreign Application Priority Data
Oct. 27, 2000 (DE) .......................... 100 53 441

(51) Int. Cl.[7] ................................. F16K 7/14
(52) U.S. Cl. ......................... 137/605; 251/61.2
(58) Field of Search .......................... 137/606, 597, 137/607, 605; 251/61.2

(56) References Cited

U.S. PATENT DOCUMENTS 4,558,715 A * 12/1985 Walton et al. ............... 137/99
4,597,412 A * 7/1986 Stark ........................... 137/606
4,703,913 A * 11/1987 Hunkapiller ................ 251/61.1

* cited by examiner

Primary Examiner—Stephen M. Hepperle
(74) Attorney, Agent, or Firm—Jacobson Holman PLLC

(57) ABSTRACT

An apparatus for the supply or branching off of a secondary flow into or out of a main flow of a medical fluid, including a fluid guide body in which at least one main passage open to one side and at least one secondary passage opening into the main passage are provided. A covering film is disposed on the fluid guide body above the open side of the main passage. The orifice of the secondary passage into the main passage can be closed by the covering film. In order to improve the haemocompatibility of the apparatus, the main passage is formed free of wake space in the region of the orifice of the secondary passage. To reduce flow losses, the secondary passage in the main passage has a streamlined outer contour in accordance with the invention corresponding to the flow direction of the main flow in the main passage. The orifice of the secondary passage is vertically coincident with the adjacent rims of the main passage so that the secondary passage can be closed by a planar valve plunger by pressing on the covering film.

31 Claims, 2 Drawing Sheets

DISPOSABLE CASSETTE HAVING A SEALING MEMBRANE AND A VALVE ACTUATOR THEREFOR

FIELD OF THE INVENTION

The present invention relates to an apparatus for the supply and/or branching of a secondary flow into and/or out of a main flow of a medical fluid comprising a fluid guidance body in which at least one main passage open to one side and at least one secondary passage opening into the main passage are provided and comprising a covering film which is disposed above the open side of the main passage on the fluid guidance body, with the opening of the secondary passage into the main passage being closable by the covering film. The invention further relates to a valve actuator for such an apparatus having a main plunger surface to press on the covering film at the edges of the main passage and a secondary plunger surface to press the covering film onto the opening of the secondary passage.

BACKGROUND OF THE INVENTION

So-called disposable cassettes of the membrane type are known, for example from WO 97/09074, in which medical fluids such as dialysis fluid flows into passages open to one side. The passage walls and the surfaces disposed between the passages are formed by a cassette body made as a rule in injection moulding. The passages open to one side are sealed by a covering film which is placed on, for example by being welded on along the passage edges or by pressing on, optionally onto passage edges made in an elevated manner.

A machine into which such a disposable cassette is inserted as a rule includes the actuating system for measuring functions, pump functions and valve functions and areally clamps the cassette together with the covering film disposed thereon. The edge layer of the surface on the machine side which lies on the covering film consists as a rule of an elastomer.

In particular with disposable cassettes which are part of an extra-corporeal blood circulation for extra-corporeal blood treatment, the requirement exists in a technical process respect that alternatively fluids such as infusion solutions, medicines, heparin, substituate and the like should be dosed in or fluid samples taken out of the passages. Valve positions are required for this purpose in order to connect the main passage, through which the medical fluid flows, to a corresponding secondary passage. This secondary passage is regularly closed since the dosing in or sampling only take a short time.

Such devices are subject to a variety of demands which have not yet been satisfactorily solved by the prior art. Generally, the functions to be met should be achieved with a compact arrangement. When the secondary passage is transposed into the main passage, however, problems result with respect to a low turbulence and low resistance flow of the medical fluid in the main passage, in particular when this is blood. Furthermore, the covering film in known arrangements tends to fatigue as a result of the secondary passage being kept closed over a long time.

SUMMARY OF THE INVENTION

It is therefore the underlying object of the present invention to provide an improved apparatus of the kind first given and an improved valve actuator of the kind first given, to avoid the disadvantages of the prior art and to further develop these in an advantageous manner. The dosing in and the sampling should preferably be made possible in a securely closing and low wear manner with a simple, compact and low cost arrangement without lasting interference to the flow relationships of the medical fluid.

This object is solved in accordance with the invention by an apparatus for supplying and/or branching off of a secondary flow into and/or out of a main flow of a medical fluid, which includes a fluid guide body, in which at least one main passage open to the side and at least one secondary passage opening into the main passage are provided. A covering film is disposed on the fluid guide body above the open side of the main passage, and the orifice of the secondary passage into the main passage can be closed by the covering film. The secondary passage is formed such that the main passage is substantially free of wake space in the region of the orifice of the secondary passage. The said object is solved in accordance with the invention by a valve actuator for the apparatus which includes a main plunger surface to press the covering film onto the rims of the main passage and a secondary plunger surface to press the covering film onto the orifice of the secondary passage, and wherein the main plunger surface and the secondary plunger surface are in the same plane.

The secondary passage, its orifice and the main passage are therefore designed in a flow-favourable manner such that a main passage flow which is free of wake space arises in the region of the orifice of the secondary passage and does not characteristically differ from the flow in the valve-free sections of the main passage. These flow qualities substantially improve the haemocompatibility of the apparatus.

In order to also achieve a low vortex and low resistance flow of the medical liquid in the main passage in the region of the secondary passage feed, the outside of the wall of the secondary passage section located in the main passage advantageously has a rounded shape favourable for flow and free of corners or edges which cause wake spaces and vortexes. The outside of the secondary passage section located in the main passage can in particular have a streamlined form in accordance with the flow direction of the main flow in the main passage. "Streamlined form" is here understood to mean a shape with a favourable circulation with which separations and vortexes or turbulences are effectively reduced and, in the ideal case, fully prevented. Unlike an only circular cross-sectional shape, vortexes and bubbles are effectively prevented by the streamlined shape and a laminar circulation of the secondary passage disposed in the main passage achieved. The flow resistance can be kept small despite the fact that the secondary passage extends in the main passage. The outer contour of the secondary passage is in particular of streamlined shape such that an eddy-free and laminar circulation is ensured which does not characteristically differ from the flow in the valve-free main passage sections. These flow qualities contribute in particular to the haemocompatibility of the apparatus for the event that blood flows through the main passage.

The ratio of the section length to the section width of the streamlined shape can generally be selected differently and matched to the circumstances of the main passage flow. In accordance with a preferred embodiment, the extent of the outside contour of the secondary passage located in the main passage in the main flow direction is at least twice as large as the extent of the outside contour transverse to the main flow direction.

In a further development of the invention, the outside contour of the secondary passage has an acutely tapering separation edge at the leading side and the trailing side, at least at the trailing side. The outside contours of the secondary passage can have a curvature continuously. The separation edge itself can also be rounded. The leading edge can be designed much rounder than the trailing edge, as is known from hydrofoil sections or drop sections. A laminar circulation is maintained in this way and connected to the advantage that the rounded leading edge offers fewer possibilities for stringy or sticky fluid components of the main flow to stick at the leading edge. A symmetrical design of the leading edge and the trailing edge can be advantageous if the flow in the main passage should run through this in changing directions.

In accordance with a preferred embodiment of the invention, the fluid guide body is characterised in that the orifice of the secondary passage into the main passage is substantially disposed in the plane set by the adjacent rims of the main passage. The end of the secondary passage at the orifice side is vertically coincident with the passage rims in the main passage and is thus in the plane of the covering film when this is stretched from the passage rims over the main passage. The covering film does not need to be pressed into the main passage in order to close the secondary passage. No impairment of the main flow takes place with a closed secondary passage. Fatigue of the covering film is substantially reduced and almost precluded since no stretching of the film is necessary in order to press this onto the secondary passage orifice. At the same time, the covering film can be placed over the main passage tautly and free of creases, whereby closing problems due to creases in the covering film are avoided.

In a further development of the invention, the orifice of the secondary passage into the main passage forms a planar, flat valve seat. Misalignments between the passage orifice and the valve plunger on the machine side thereby become insignificant and generous positioning tolerances are made possible between the disposable and the machine actuator, which reduces the costs due to reduced accuracy demands and increases the closing security.

In accordance with a preferred embodiment of the invention, the longitudinal axis of the secondary passage opens perpendicularly onto the flow direction of the main flow and in particular perpendicular to the covering film. The secondary passage can form a funnel in the main passage which extends from the base of the main passage up to its open side. The secondary passage comes from the rear side of the fluid guide body opposite to the open side of the main passages. Due to the side change of the secondary flow opening into the main flow, the rear side of the fluid guide body can likewise be used for flow passages which can even cross over the front-side main passages. A more effective use of the constructional space for the functions of the apparatus is thus possible. The secondary passage can be guided at the rear of the body either coaxially or at an angle into another flow tube which can be made in a technical injection moulding manner in a suitable embodiment. This other end of this tube can be formed as a male connector or as a hose permanent connection connector.

The section of the secondary passage which is in the main passage can be arranged at a different position there. It can extend along a wall of the main passage so that only a part of the secondary passage wall projects over the main passage wall. With such an embodiment, only this part of the secondary passage outer contour is accordingly formed in streamlined manner. The projecting secondary passage wall forms a streamlined half-section.

To facilitate the production and the sealing of the passages, it is preferably provided that the seal line around the orifice of the secondary passage, along which the secondary passage can be closed by the covering film, is spaced from the seal lines along which the main passage can be closed by the covering film.

In accordance with a preferred embodiment of the invention, the secondary passage extends in self-supporting manner in the main passage. The secondary passage in the main passage is in particular arranged symmetrically relative to this. The secondary passage is flowed around in the main passage in a favourably flow similar to a bridge support or an island. Since the orifice of the secondary passage contacts the wall of the main passage formed by the covering film and thus closes, the main passage flow is not influenced by the secondary passage orifice in its closed state as this is not flowed around at all by the main passage flow.

The main passage is preferably shaped in a favourable flow manner around the secondary passage, in particular such that the flow cross-section in the main passage also remains approximately constant in the region of the secondary passage which opens in. Changes in the flow speed are avoided in this way. When blood is the fluid flowing in the main passage, it has moreover surprisingly been shown to be favourable for the flow cross-section in the main passage to be somewhat larger in the region of the opening secondary passage than in the main passage before and after this. In this respect, an enlargement of 40% is advantageous, in particular of 25%.

As a consequence of the vertically coincident arrangement of the secondary passage orifice to the main passage rims, a common planar plunger surface can be provided as the valve plunger to press on the covering film which presses the covering film both onto the rims of the main passage and onto the secondary passage orifice. The common, planar plunger surface allows generous positioning tolerances when setting the plunger actuator onto the covering film without reducing the closing reliability. Furthermore, the planar valve seat on the machine side means that the valve position does not make itself felt there at all geometrically and is thus neither at risk of collision nor of contamination. Furthermore, only a very slight deformation of the covering film and of the machine membrane provided on the valve actuator side results with the closed position of the valve actuator provided for most of the time. The circumstances reduce the actuating forces and the fatigue. Furthermore, a plastic deformation of the disposable film is avoided which precludes crease formation and increases the closing reliability.

In a further development of the invention, the plunger surface for the secondary passage orifice is designed movably relative to the main plunger surface for the main passage rims. In can be moved by means of an actuating part. The movability of the plunger surface section for the secondary passage orifice can be achieved by various designs of the plunger surface. A preferred embodiment consists of the whole plunger surface being formed by an elastomer plate.

The actuating part and thus the corresponding section of the plunger surface on the machine side is raised from the covering film on the fluid guide body in order to open the secondary passage orifice. In this respect, the covering film is raised from the orifice of the secondary passage so that the secondary passage is brought into flow communication with the main passage. The lifting of the covering film takes place automatically as a result of an overpressure of the main flow or of the secondary flow. In a further development of the invention, a vacuum can also be disposed between the plunger surface of the valve plunger and the covering film so that the covering film is actively raised on the moving away of the plunger surface. In this way, the fluid connection between the secondary passage and the main passage can be controlled independently of pressure relationships in the cassette-side flow passages.

Particular advantages result in the use of the above-said apparatus in conjunction with blood, that is in the supply of a medical fluid into a bloodstream and/or the sampling from a bloodstream. The streamlined shape of the secondary passage prevents the stalling of the bloodstream in wake spaces or flow shadows behind the secondary passage and a blood-damaging formation of turbulence.

The apparatus of the invention for the feed and/or branching off of a secondary flow into and/or out of a main flow is used particularly advantageously as part of an extra-corporeal blood circulation for extra-corporeal blood treatment. Such a blood treatment can, for example, comprise haemodialysis, haemofiltration, blood cell separation or blood adsorption. In this application, the apparatus is advantageously designed as a disposable for throw-away use. The valve actuator of the invention is in this case usually part of the blood treatment machine which controls the flows of the fluids involved.

BRIEF DESCRIPTION OF THE DRAWINGS

The invention is described in more detail in the following by means of a preferred embodiment and with reference to the drawing. The drawings show.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The fluid guide body shown in the Figures with the covering film lying thereon can generally be used in chemo-pharmaceutical process technology as a disposable component for insertion into hose systems or as a permanently used membrane valve. The fluid guide body having the associated covering film is, however, in particular a disposable cassette of the membrane type for medical fluids, preferably for blood for the extra-corporeal treatment of the blood such as haemodialysis.

Figure 1:
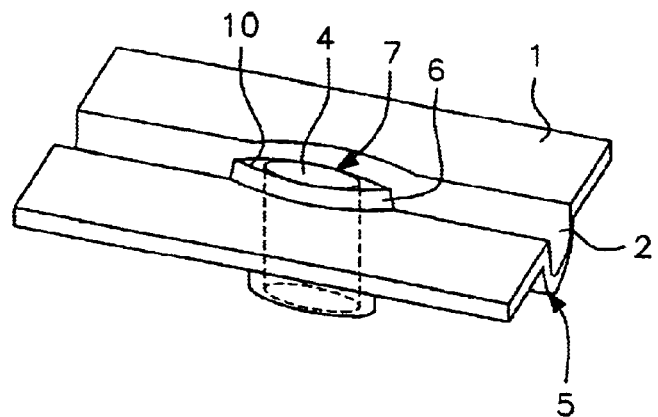
FIG. 1: a perspective view of a fluid guide body having an open main passage and a secondary channel opening therein in accordance with a preferred embodiment of the invention in a sectional representation.

As FIG. 1 shows, the fluid guide body 1, which can be made of plastic and in particular be injection moulded, has a main passage 2 which is integrally worked into the fluid guide body 1 and is open to one side. The open side of the main passage 2 is closed by a covering film 3 which is not shown in FIG. 1 and which is formed in particular as an elastic membrane made of plastic, as will still be explained in conjunction with FIGS. 2 and 3.

Figure 2:
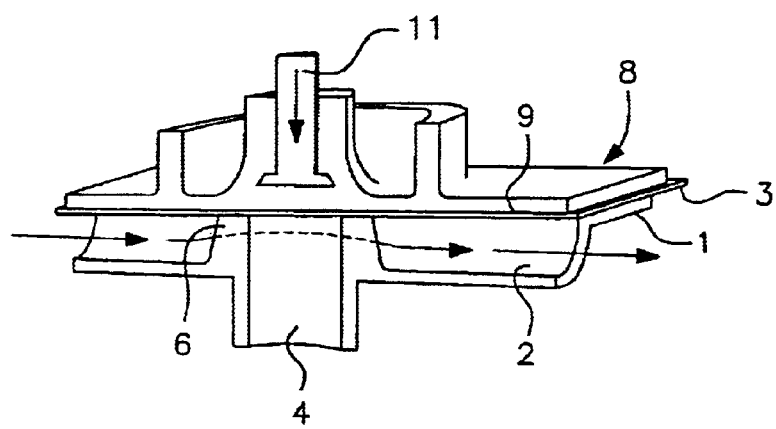
FIG. 2 a perspective view of the fluid guide body of FIG. 1 in a part section, wherein a covering film is pressed onto the fluid guide body by means of a valve actuator and closes the secondary passage.

The fluid guide body 1 further has a secondary passage 4 which leads away from the rear side of the fluid guide body 1, which is remote from the open side of the main passage 2, onto the opposite front side of the fluid guide body 1 and opens there into the main passage 2. As FIG. 2 shows, the secondary passage 4 passes through the base 5 of the main passage. The secondary passage 4 extends in the main passage 2 in the form of a volcano-like funnel 6 whose height corresponds to the depth of the main passage so that an orifice 7 of the secondary passage 4 is arranged vertically coincident with the rims of the main passage 2.

The secondary passage 4 is positioned symmetrically in the centre of the main passage 2 and extends perpendicularly to the longitudinal direction of the main passage 2. The planar designed orifice 7 is in the plane which is set up by the rims of the main passage 2.

As FIG. 1 shows, the funnel 6 has a streamlined cross-section. In more precise terms, the outside of the wall of the secondary passage 4 in the main passage 2 is formed in streamlined manner, with the longitudinal axis of the streamlined shape corresponding to the longitudinal axis of the main passage 2. Vortexes, turbulences and an increased flow resistance are thereby avoided at the secondary passage. The medical fluid flowing through the main passage 2 can flow past the secondary passage 4 in laminar fashion.

As FIG. 1 shows, the contours of the main passage 2 are also formed extending in streamlined fashion around the secondary passage 4. The side walls of the main passage 2 opposite the funnel 6 bulge in streamlined fashion around the funnel 6 so that the fluid flow forking around the funnel 6 finds approximately the same flow cross-section and can flow past this without any larger speed changes.

To be able to close the open side of the secondary passage 4 and simultaneously the orifice 7 of the secondary passage 4, the covering film 3, which can be welded or connected in another way to the fluid guide body 1, lies on the fluid guide body 1. To seal the main passage 2, the covering film 3 can be welded to the fluid guide body 1 along the rims of the main passage 2. The sealing can, however, also be effected by pressing the covering film 3 along the rims of the main passage 2 by means of a valve plunger 8.

The valve plunger 8 has a continuous, planar plunger surface 9 which is formed by an elastic machine membrane preferably made of an elastomer. Due to the vertically coincident arrangement of the orifice 7 with the rims of the main passage 2, the secondary passage 4 can be closed without stretching of the covering film 3, if the covering film 3 is pressed overall onto the fluid guide body 1. The orifice 7 is formed for this purpose as a planar valve seat 10 which is in the plane set up by the rims of the main passage 2 and forms the front end of the funnel 6.

FIG. 2 shows the closed state of the secondary passage 4. The plunger surface 9 is pressed overall onto the fluid guide body 1. Additional pressure can preferably be applied by an actuating part 11 in the region of the orifice 7 of the secondary passage 4 in order to achieve a reliable sealing of the secondary passage 4.

Figure 3:
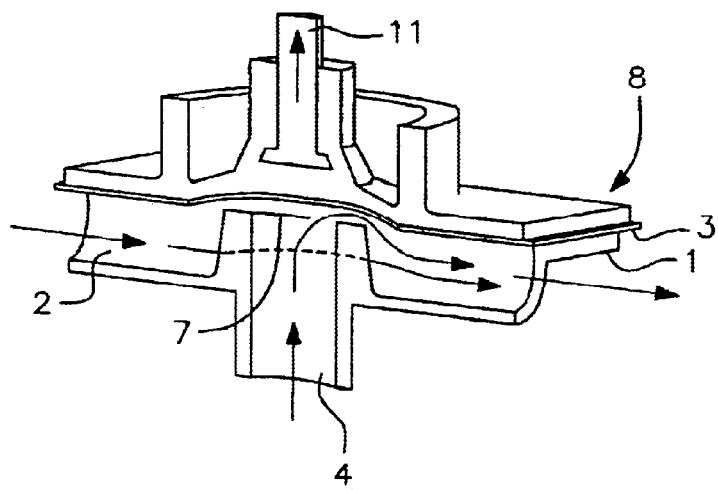
FIG. 3: perspective view similar to FIG. 2, wherein the secondary passage is represented in its open position.

To open the secondary passage 4, the actuating part 11, which is connected to the plunger surface 9 in the region of the secondary passage orifice 7, is moved away from the fluid guide body 1. The plunger surface 9 is thereby raised from the orifice 7 of the secondary passage 4 in the region thereof. As FIG. 3 shows, the plunger surface 9 thereby deforms, which is allowed by the design of the same as an elastic membrane.

The covering film 3 also lifts off the orifice 7 of the secondary passage 4 due to the raising of the plunger surface 9. The pressure of the flow in the main passage 2 presses the covering film 3 away from the orifice 7. Optionally, this can also be supported actively by the interposition of a vacuum between the plunger surface 9 and the covering film 3, which is helpful in particular when a sample should be sucked from the fluid flow in the main passage 2 through the secondary passage 4.

When the orifice 7 lifts, the covering film 3 stretches elastically. The deformation is here very low, however. It is in particular not plastic so that a formation of creases in the subsequent re-closing of the orifice 7 is prevented. As FIG. 3 shows, the secondary passage 4 is in flow communication with the main passage 2 in the raised state of the covering film 3.

Figure 4:
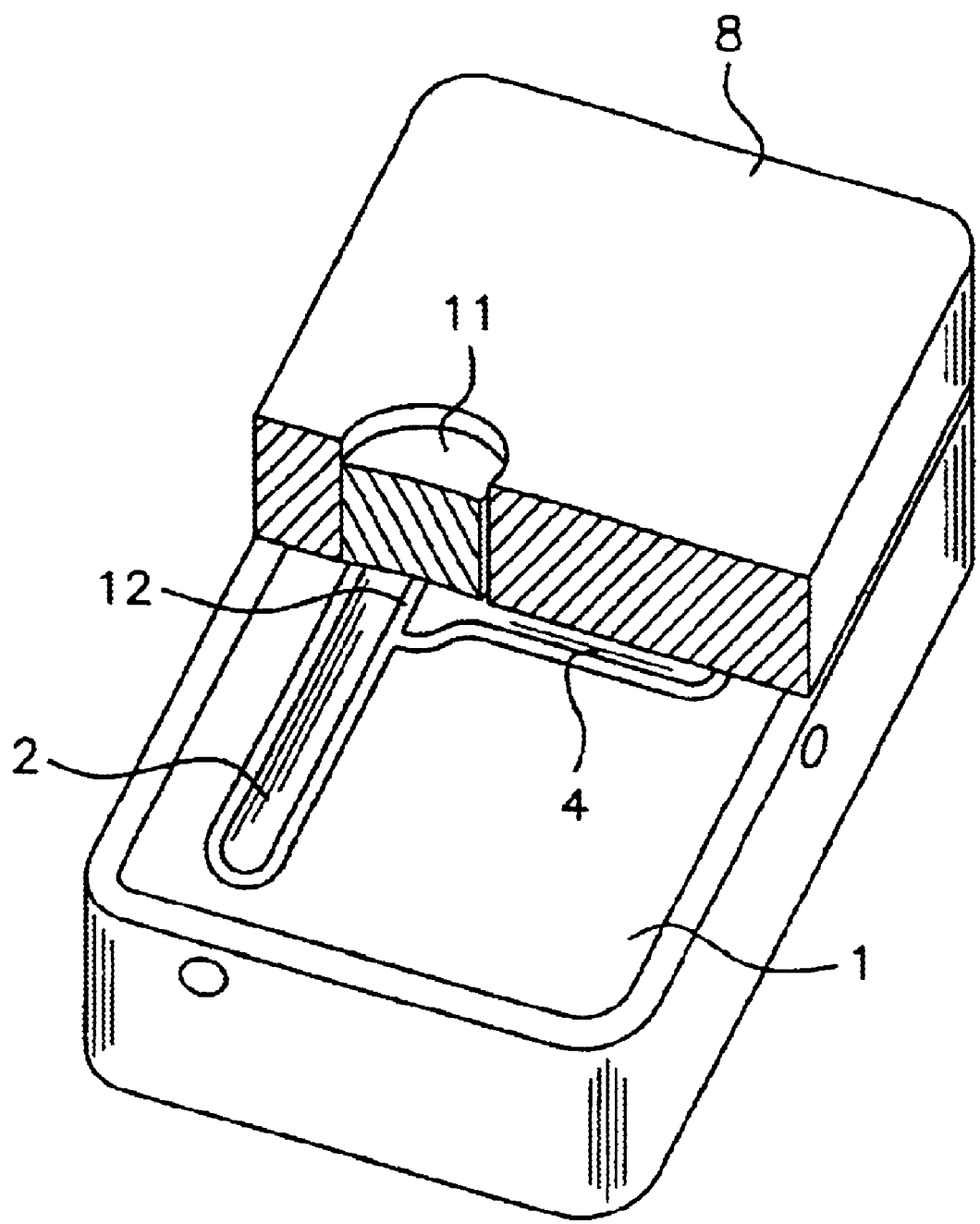
FIG. 4: a perspective view of a fluid guide body having an open main passage and a secondary passage opening into this in accordance with a further preferred embodiment of the invention.

FIG. 4 shows a further embodiment of the invention in which corresponding parts are marked with the same reference numerals as in the previously described embodiment. The secondary passage 4 does not open into the main passage 2 in the form of a volcano-like funnel in this embodiment. It is rather the case that the main passage 2 and the secondary passage 4, which are both—the secondary passage 4 at least partly—formed as an open groove in the fluid guide body 1, are only separated from one another by a web 12 which forms a side wall of the main passage 2 and constantly continues this towards the adjoining regions (cf. FIG. 4). The secondary passage extends in the embodiment shown perpendicularly towards the main passage 2, with the cross-section of the secondary passage 4 preferably extending in delta shape towards the separating web 12.

The raising of the elastomer covering film (and also possibly of the elastomer machine plunger covering membrane) is similar to the opening of lips: since the film and the membrane may not be overstretched, in order to be able to close again later without creases, the opening stroke is relatively small and the opening width relatively big. This is the reason for the delta-shaped expansion of the normally narrow secondary passage.

The connection of the secondary passage 4 to the main passage 2 is controlled by the covering film 3 which lies on the fluid guide body 1 and which spans the open sides of the secondary passage 4 and the main passage 2. The covering film is not shown in FIG. 4. The covering film can be welded onto the fluid guide body 1 around the main passage 2 while leaving out the separating web 12 or around the secondary passage 4. However, as previously described, it can also be pressed against the surface of the fluid guide body 1 by a valve plunger which can be formed by a machine block. To bring the secondary passage 4 into flow communication with the main passage 2, a valve actuator or the actuator part 11 is provided which sits on the fluid guide body 1 in the region of the web 12 and presses the covering film onto the web 12. If the actuator part 11 is moved away from the fluid guide body 1, the film can be moved away from the web 12 so that the main passage 2 is brought into flow communication with the secondary passage 4 over said web 12. It is understood that the valve plunger 8 is shown in sectioned form in FIG. 4 and extends over the whole surface of the fluid guide body 1 in which the passages appear in open form.

Stationary and moving sealing zones directly bound lip rims, while in the embodiment in accordance with FIGS. 1–3, the dynamic regions are uncoupled from the static regions by the circulation passage.

In this embodiment, the main passage flow remains fully uninfluenced by the secondary passage 4 or its orifice. In the closed position, that is when the actuator part 11 is pressed onto the fluid guide body 1, no valve or no secondary passage is present from the viewpoint of the main passage flowing through so that optimum flow relationships can be achieved.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. An apparatus for supplying and/or branching off of a secondary flow into and/or out of a main flow of a medical fluid, said apparatus comprising
   a fluid guide body having at least one main passage extending therethrough and defined between two rims and being open at a side;
   at least one secondary passage;
   a covering film located on the fluid guide body spanning the open side of the main passage; and
   an opening of the at least one secondary passage being closable by the covering film and the opening of the at least one secondary passage being vertically coincident with the rims of the at least one main passage; and
   an outer contour of the secondary passage being disposed in the main passage and having a streamlined shape corresponding to a flow direction of the main flow in the main passage.

2. The apparatus in accordance with claim 1, wherein the outer contour of the secondary passage disposed in the main passage has at least one of an acutely tapering separation edge and a rounded leading edge.

3. The apparatus in accordance with claim 1, wherein the opening of the secondary passage has a planar, flat valve seat.

4. The apparatus in accordance with claim 1, wherein a longitudinal axis of the secondary passage opens perpendicularly to a flow direction of the main flow and perpendicular to the covering film.

5. The apparatus in accordance with claim 1, wherein the secondary passage is guided on a rear side of the fluid guide body opposite the open side of the main passage.

6. The apparatus in accordance with claim 1, wherein the covering film consists of plastic.

7. The apparatus in accordance with claim 1, further comprising a valve actuator having a main plunger surface to press the covering film onto the rims of the main passage and a secondary plunger surface to press the covering film onto the opening of the secondary passage, wherein the main plunger surface and the secondary plunger surface are in the same plane.

8. The apparatus in accordance with claim 7, wherein the main plunger surface and the secondary plunger surface are formed by a common planar plunger surface.

9. An apparatus for supplying and/or branching off of a secondary flow into and/or out of a main flow of a medical fluid, said apparatus comprising
   a fluid guide body having at least one main passage open at a side and at least one secondary passage opening into the main passage;
   a covering film located on the fluid guide body above the open side of the main passage;

an orifice of the at least one secondary passage into the main passage being closable by the covering film; and the secondary passage being formed such that the main passage is substantially free of wake space in a region of the orifice of the secondary passage;

a main plunger surface pressing the covering film onto rims of the side of the main passage and a secondary plunger surface pressing the covering film onto the orifice of the secondary passage, wherein the main plunger surface and the secondary plunger surface are in a same plane; and an outer contour of the secondary passage being disposed in the main passage and having a streamlined share corresponding to a flow direction of the main flow in the main passage.

10. The apparatus in accordance with claim 9, wherein a longitudinal axis of the secondary passage opens perpendicularly to a flow direction of the main flow and perpendicular to the covering film.

11. The apparatus in accordance with claim 9, wherein the covering film consists of plastic.

12. An apparatus for supplying and/or branching off of a secondary flow into and/or out of a main flow of blood, said apparatus comprising a fluid guide body having at least one main passage extending therethrough and defined between two rims and being open at a side;

at least one secondary passage opening into the main passage;

a covering film located on the fluid guide body spanning the open side of the main passage;

an orifice of the at least one secondary passage being closable by the covering film; and an outer contour of the secondary passage being disposed in the main passage and having a rounded leading edge at an upstream side of blood flow through the main passage.

13. An apparatus for supplying and/or branching off of a secondary flow into and/or out of a main flow of a medical fluid, said apparatus comprising a fluid guide body having at least one main passage extending therethrough and defined between two rims and being open at a side;

at least one secondary passage opening into the main passage;

a covering film located on the fluid guide body spanning the open side of the main passage; and an orifice of the at least one secondary passage being closable by the covering film, the main passage being shaped around the secondary passage with a constant flow cross-section such that a flow cross-action in the main passage is approximately constant both upstream and downstream of the secondary passage and around said secondary passage.

14. An apparatus for supplying and/or branching off of a secondary flow into and/or out of a main flow of a medical fluid, said apparatus comprising a fluid guide body having a main passage extending therethrough and being open at a side and a secondary passage formed in the fluid guide body being open at a side and separated from the main passage by a side wall of the main passage;

a covering film located on the fluid guide body spanning the open side of the main passage and the open side of the secondary passage; and the secondary passage opening into the main passage across the side wall of the main passage when the covering film is lifted and the secondary passage being prevented from opening into the main passage by the covering film when the covering film rests on the side wall of the main passage;

the fluid guide body being a disposable cassette.

15. An apparatus for supplying and/or branching off of a secondary flow into and/or out of a main flow of a medical fluid, said apparatus comprising a fluid guide body having at least one main passage extending therethrough and defined between two rims and being open at a side;

at least one secondary passage;

a covering film located on the fluid guide body spanning the open side of the main passage; and an opening of the at least one secondary passage being closable by the covering film and the opening of the at least one secondary passage being vertically coincident with the rims of the at least one main passage;

the secondary passage forming a funnel in the main passage which extends from a base of the main passage up to the open side.

16. An apparatus for supplying and/or branching off of a secondary flow into and/or out of a main flow of a medical fluid, said apparatus comprising a fluid guide body having at least one main passage extending therethrough and defined between two rims and being open at a side;

at least one secondary passage;

a covering film located on the fluid guide body spanning the open side of the main passage; and an opening of the at least one secondary passage being closable by the covering film and the opening of the at least one secondary passage being vertically coincident with the rims of the at least one main passage;

the secondary passage being disposed symmetrically in the main passage.

17. An apparatus for supplying and/or branching off of a secondary flow into and/or out of a main flow of a medical fluid, said apparatus comprising a fluid guide body having at least one main passage extending therethrough and defined between two rims and being open at a side;

at least one secondary passage;

a covering film located on the fluid guide body spanning the open side of the main passage; and an opening of the at least one secondary passage being closable by the covering film and the opening of the at least one secondary passage being vertically coincident with the rims of the at least one main passage;

the main passage being shaped around the secondary passage such that a flow cross-section in the main passage is approximately constant.

18. An apparatus for supplying and/or branching off of a secondary flow into and/or out of a main flow of a medical fluid, said apparatus comprising a fluid guide body having at least one main passage extending therethrough and defined between two rims and being open at a side;

at least one secondary passage;

a covering film located on the fluid guide body spanning the open side of the main passage; and an opening of the at least one secondary passage being closable by the covering film and the opening of the at least one secondary passage being vertically coincident with the rims of the at least one main passage;

the fluid guide body being a disposable cassette.

19. An apparatus for supplying and/or branching off of a secondary flow into and/or out of a main flow of a medical fluid, said apparatus comprising a fluid guide body having at least one main passage extending therethrough and defined between two rims and being open at a side;

at least one secondary passage;

a covering film located on the fluid guide body spanning the open side of the main passage;

an opening of the at least one secondary passage being closable by the covering film and the opening of the at least one secondary passage being vertically coincident with the rims of the at least one main passage; and a valve actuator having a main plunger surface to press the covering film onto the rims of the main passage and a secondary plunger surface to press the covering film onto the opening of the secondary passage, the main plunger surface and the secondary plunger surface being in the same plane, the main plunger surface and the secondary plunger surface being formed by a common planar plunger surface, and the secondary plunger surface being movable relative to the main plunger surface and an actuator part being provided for actuation of the secondary plunger surface.

20. An apparatus for supplying and/or branching off of a secondary flow into and/or out of a main flow of a medical fluid, said apparatus comprising a fluid guide body having at least one main passage extending therethrough and defined between two rims and being open at a side;

at least one secondary passage;

a covering film located on the fluid guide body spanning the open side of the main passage;

an opening of the at least one secondary passage being closable by the covering film and the opening of the at least one secondary passage being vertically coincident with the rims of the at least one main passage; and a valve actuator having a main plunger surface to press the covering film onto the rims of the main passage and a secondary plunger surface to press the covering film onto the opening of the secondary passage, the main plunger surface and the secondary plunger surface being in the same plane, the secondary plunger surface and the main plunger surface being formed by an elastomer plate.

21. An apparatus for supplying and/or branching off of a secondary flow into and/or out of a main flow of a medical fluid, said apparatus comprising a fluid guide body having at least one main passage open at a side and at least one secondary passage opening into the main passage;

a covering film located on the fluid guide body above the open side of the main passage;

an orifice of the at least one secondary passage into the main passage being closable by the covering film; and the secondary passage being formed such that the main passage is substantially free of wake space in a region of the orifice of the secondary passage; and a main plunger surface pressing the covering film onto rims of the side of the main passage and a secondary plunger surface pressing the covering film onto the orifice of the secondary passage, wherein the main plunger surface and the secondary plunger surface are in a same plane;

the outer contour of the secondary passage being disposed in the main passage and having at least one of an acutely tapering separation edge and a rounded leading edge.

22. An apparatus for supplying and/or branching off of a secondary flow into and/or out of a main flow of a medical fluid, said apparatus comprising a fluid guide body having at least one main passage open at a side and at least one secondary passage opening into the main passage;

a covering film located on the fluid guide body above the open side of the main passage;

an orifice of the at least one secondary passage into the main passage being closable by the covering film; and the secondary passage being formed such that the main passage is substantially free of wake space in a region of the orifice of the secondary passage; and a main plunger surface pressing the covering film onto rims of the side of the main passage and a secondary plunger surface pressing the covering film onto the orifice of the secondary passage, wherein the main plunger surface and the secondary plunger surface are in a same plane;

the orifice of the secondary passage extending into the main passage and having a planar, flat valve seat.

23. An apparatus for supplying and/or branching off of a secondary flow into and/or out of a main flow of a medical fluid, said apparatus comprising a fluid guide body having at least one main passage open at a side and at least one secondary passage opening into the main passage;

a covering film located on the fluid guide body above the open side of the main passage;

an orifice of the at least one secondary passage into the main passage being closable by the covering film; and the secondary passage being formed such that the main passage is substantially free of wake space in a region of the orifice of the secondary passage; and a main plunger surface pressing the covering film onto rims of the side of the main passage and a secondary plunger surface pressing the covering film onto the orifice of the secondary passage, wherein the main plunger surface and the secondary plunger surface are in a same plane;

the orifice of the secondary passage extending into the main passage and being disposed in a plane defined by adjacent edges of the main passage.

24. An apparatus for supplying and/or branching off of a secondary flow into and/or out of a main flow of a medical fluid, said apparatus comprising a fluid guide body having at least one main passage open at a side and at least one secondary passage opening into the main passage;

a covering film located on the fluid guide body above the open side of the main passage;

an orifice of the at least one secondary passage into the main passage being closable by the covering film; and the secondary passage being formed such that the main passage is substantially free of wake space in a region of the orifice of the secondary passage; and a main plunger surface pressing the covering film onto rims of the side of the main passage and a secondary plunger surface pressing the covering film onto the orifice of the secondary passage, wherein the main plunger surface and the secondary plunger surface are in a same plane;

the secondary passage forming a funnel in the main passage and extending from a base of the main passage up to the open side.

25. An apparatus for supplying and/or branching off of a secondary flow into and/or out of a main flow of a medical fluid, said apparatus comprising a fluid guide body having at least one main passage open at a side and at least one secondary passage opening into the main passage;

a covering film located on the fluid guide body above the open side of the main passage;

an orifice of the at least one secondary passage into the main passage being closable by the covering film; and the secondary passage being formed such that the main passage is substantially free of wake space in a region of the orifice of the secondary passage; and a main plunger surface pressing the covering film onto rims of the side of the main passage and a secondary plunger surface pressing the covering film onto the orifice of the secondary passage, wherein the main plunger surface and the secondary plunger surface are in a same plane;

the secondary passage being disposed symmetrically in the main passage.

26. An apparatus for supplying and/or branching off of a secondary flow into and/or out of a main flow of a medical fluid, said apparatus comprising a fluid guide body having at least one main passage open at a side and at least one secondary passage opening into the main passage;

a covering film located on the fluid guide body above the open side of the main passage;

an orifice of the at least one secondary passage into the main passage being closable by the covering film; and the secondary passage being formed such that the main passage is substantially free of wake space in a region of the orifice of the secondary passage; and a main plunger surface pressing the covering film onto rims of the side of the main passage and a secondary plunger surface pressing the covering film onto the orifice of the secondary passage, wherein the main plunger surface and the secondary plunger surface are in a same plane;

the main passage being shaped around the secondary passage such that a flow cross-section in the main passage is approximately constant.

27. An apparatus for supplying and/or branching off of a secondary flow into and/or out of a main flow of a medical fluid, said apparatus comprising a fluid guide body having at least one main passage open at a side and at least one secondary passage opening into the main passage;

a covering film located on the fluid guide body above the open side of the main passage;

an orifice of the at least one secondary passage into the main passage being closable by the covering film; and the secondary passage being formed such that the main passage is substantially free of wake space in a region of the orifice of the secondary passage; and a main plunger surface pressing the covering film onto rims of the side of the main passage and a secondary plunger surface pressing the covering film onto the orifice of the secondary passage, wherein the main plunger surface and the secondary plunger surface are in a same plane;

the secondary passage being guided on a rear side of the fluid guide body opposite the open side of the main passage.

28. An apparatus for supplying and/or branching off of a secondary flow into and/or out of a main flow of a medical fluid, said apparatus comprising a fluid guide body having at least one main passage open at a side and at least one secondary passage opening into the main passage;

a covering film located on the fluid guide body above the open side of the main passage;

an orifice of the at least one secondary passage into the main passage being closable by the covering film; and the secondary passage being formed such that the main passage is substantially free of wake space in a region of the orifice of the secondary passage; and a main plunger surface pressing the covering film onto rims of the side of the main passage and a secondary plunger surface pressing the covering film onto the orifice of the secondary passage, wherein the main plunger surface and the secondary plunger surface are in a same plane;

the fluid guide body being a disposable cassette.

29. An apparatus for supplying and/or branching off of a secondary flow into and/or out of a main flow of a medical fluid, said apparatus comprising a fluid guide body having at least one main passage open at a side and at least one secondary passage opening into the main passage;

a covering film located on the fluid guide body above the open side of the main passage;

an orifice of the at least one secondary passage into the main passage being closable by the covering film; and the secondary passage being formed such that the main passage is substantially free of wake space in a region of the orifice of the secondary passage; and a main plunger surface pressing the covering film onto rims of the side of the main passage and a secondary plunger surface pressing the covering film onto the orifice of the secondary passage, wherein the main plunger surface and the secondary plunger surface are in a same plane;

the main plunger surface and the secondary plunger surface being formed by a common planar plunger surface.

30. An apparatus for supplying and/or branching off of a secondary flow into and/or out of a main flow of a medical fluid, said apparatus comprising a fluid guide body having at least one main passage open at a side and at least one secondary passage opening into the main passage;

a covering film located on the fluid guide body above the open side of the main passage;

an orifice of the at least one secondary passage into the main passage being closable by the covering film; and the secondary passage being formed such that the main passage is substantially free of wake space in a region of the orifice of the secondary passage; and a main plunger surface pressing the covering film onto rims of the side of the main passage and a secondary plunger surface pressing the covering film onto the orifice of the secondary passage, wherein the main plunger surface and the secondary plunger surface are in a same plane;

the secondary plunger surface being movable relative to the main plunger surface and an actuator part being provided for actuation of the secondary plunger surface.

31. An apparatus for supplying and/or branching off of a secondary flow into and/or out of a main flow of a medical fluid, said apparatus comprising a fluid guide body having at least one main passage open at a side and at least one secondary passage opening into the main passage;

a covering film located on the fluid guide body above the open side of the main passage;

an orifice of the at least one secondary passage into the main passage being closable by the covering film;

the secondary passage being formed such that the main passage is substantially free of wake space in a region of the orifice of the secondary passage; and a main plunger surface pressing the covering film onto rims of the side of the main passage and a secondary plunger surface pressing the covering film onto the orifice of the secondary passage, wherein the main plunger surface and the secondary plunger surface are in a same plane;

the secondary plunger surface and the main plunger surface being formed by an elastomer plate.

* * * * *